United States Patent [19]

Barta et al.

[11] 4,124,449
[45] Nov. 7, 1978

[54] METHOD AND APPARATUS FOR BACTERIAL MICROSCOPY

[76] Inventors: Kent S. Barta, 721 Olive St., St. Louis, Mo. 63101; Jerome A. Gross, 6304 S. Rosebury, Clayton, Mo. 63105

[21] Appl. No.: 765,938

[22] Filed: Feb. 7, 1977

[51] Int. Cl.$^2$ .............................................. C12K 1/10
[52] U.S. Cl. ............................ 195/139; 195/103.5 M; 350/95
[58] Field of Search ................. 195/127, 139, 103.5 M; 350/95

[56] References Cited

U.S. PATENT DOCUMENTS

| | | | |
|---|---|---|---|
| 2,879,207 | 3/1959 | Poitras | 195/139 |
| 3,295,686 | 1/1967 | Krueger | 195/127 |
| 3,386,585 | 6/1968 | Weyand et al. | 195/127 |
| 3,783,105 | 1/1974 | Moyer et al. | 195/127 |
| 3,844,895 | 10/1974 | Rose et al. | 195/139 |
| 3,963,355 | 6/1976 | Aldridge, Jr. et al. | 195/103.5 M |

*Primary Examiner*—Alvin E. Tanenholtz

[57] ABSTRACT

The present invention provides a method and apparatus for microscopic examination of samples containing bacteria in low numbers and which require precise staining procedures for visualization and counting. A slide has a filter assembly through which the bacterial suspension is filtered onto a filter membrane. A chamber adjacent to said filter, by sliding, delivers to the filter surface with simultaneous mixing, an optimum amount of bacterial dye at the proper concentration. The upper portion of the sliding chamber then fits over the filter membrane to form an incubation chamber. After incubation, the bacteria so stained are easily washed and conveniently further prepared for microscopic inspection.

By use of this method and apparatus, all of the complex steps of the fluorescent antibody technique can be simply performed.

8 Claims, 4 Drawing Figures

METHOD AND APPARATUS FOR BACTERIAL MICROSCOPY

BACKGROUND OF THE INVENTION

Bacteria of various genera are ubiquitously present and grow luxuriantly in organic substrates such as foodstuffs. To determine the level of such organisms, aqueous infusions of foodstuffs such as processed meat and grain are prepared and aliquots of serial dilutions thereof are subjected to conventional plating and culture techniques. Bacterial colonies appear upon the agar surface of ordinary Petrie plates and are counted. This method, however, requires a 24 to 48 hour incubation period, which is too long a delay for commercial production.

A method for eliminating the long incubation period, utilized for testing soil samples and for medical diagnoses, is the fluorescent antibody technique. Where samples for testing are relatively free of other organic matter, the procedure requires merely the incubation of fixed cells with a solution containing specific serum antibody conjugated to a dye molecule which fluoresces at a specific wave length of ultraviolet light. Bacteria so stained are easily visible under an ordinary dark field microscope.

For analysis of complex organic matter, the techniques for immunofluorescence are complicated and require expensive equipment including a microscope designed for epifluorescent visualization. To the knowledge of applicants, no apparatus has heretofore been used or suggested which so simplifies this technique as to make it practicable and inexpensive for routine use in food testing and other industrial applications.

SUMMARY OF THE INVENTION

A principle object of the present invention is to provide apparatus by which bacteria suspended in low numbers in an infusion containing particulate organic matter may be rapidly enumerated. The present invention is particularly suitable for use in fluorescent antibody and other cell labeling techniques. Concentration of bacteria, staining, incubation, washing, microscopic visualization, and other steps involved in such techniques are all carried out using one piece of apparatus.

Briefly summarizing, the present apparatus is comprised of a filter mount, a filter membrane mounted therein, and a slidable delivery chamber, preferably mounted in a channel leading to the filter membrane, by which a liquid containing fluorescent antibodies or other cell labeling agents may be displaced onto the filter membrane. Bacteria, concentrated by filtration onto the surface of said filter membrane, are thereby labeled with the cell labeling agent. The slidable delivery chamber has lower surfaces which seal around the upper surface of the filter mount, thereby forming a chamber for incubation.

In the process described, a cell-labeling agent, stored frozen in the delivery chamber, is liquefied; and after a bacterial suspension is filtered onto the membrane, the liquid is delivered by moving the delivery chamber over the filter. The delivery chamber remains in this position during incubation, to serve as an incubation chamber.

DETAILED DESCRIPTION OF THE PREFERRED EMBODIMENT

Figure 1:
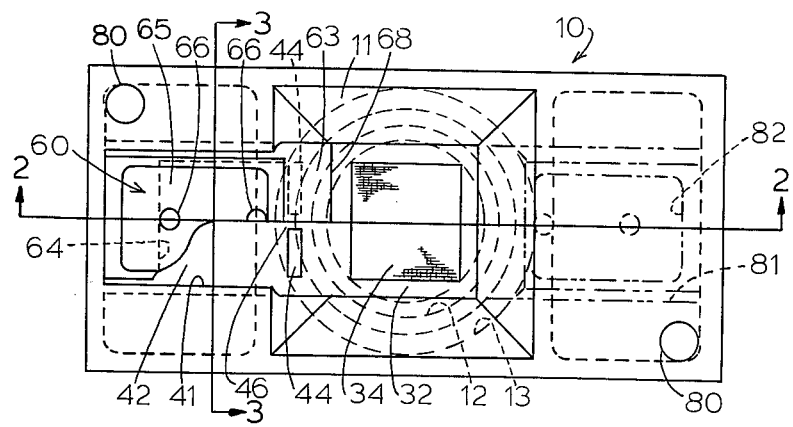
FIG. 1 is a plan view, somewhat enlarged, of apparatus for use in microscopy embodying the present invention, shown with its delivery chamber partially broken away. The phantom lines at the upper portion show the alternate use of a second similar delivery chamber.

The preferred embodiment of the present invention as shown in the drawings comprises a rectangular body structure formed preferably of molded plastic and generally designated 10, and a slidable delivery chamber, generally designated 60, is hereinafter more fully described.

A central well portion 11 of the body structure 10 is preferably square-shaped with downward leading walls on three sides, which terminate on the outer edge of a square-shaped flange-like frame portion 32. The sloping walls of the well portion 11 accommodate the objective of a microscope to be used in viewing through the frame portion 32. Below the flange-like frame portion is an upward extending cylindrical bore 12 of a diameter at least equal to the diagonal distance across the frame portion. The bore 12 extends upward as far as feasible for molding the plastic material; at its upper extremity is a partially circular seating shoulder 33 against which is positioned a circular filter membrane 34 which extends across the frame portion 32. The filter membrane 34 is firmly held against the seating shoulder 33 by a press fitted ring 35.

Formed upwardly into the structure 10 and concentrically outward from the central circular bore 12 is a radial groove 13 of such depth and shape as to accommodate the rim of a vacuum bottle (not shown), thereby to form a seal during filtration. At the outer rectangular periphery of the plastic body structure 10 is a lower exterior flange 15 to provide stability, inward of which the structure 10 may be cored.

Figure 2:
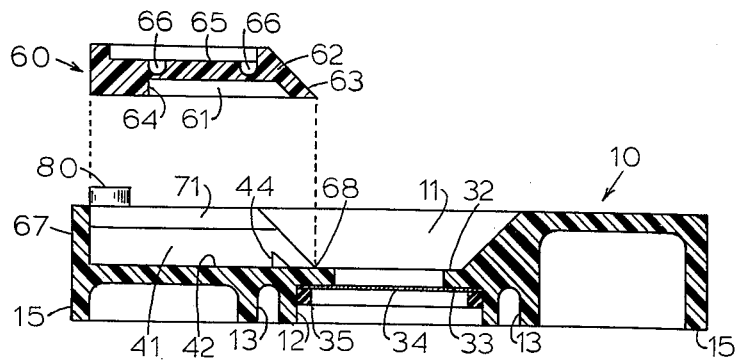
FIG. 2 is an exploded view taken along line 2—2 of FIG. 1.

One of the sloping walls of said central well portion 11 is interrupted by a channel portion 41 whose width equals that of the frame portion 32 and whose horizontal planar lower surface 42 is in the same plane as the frame portion 32 (FIG. 2). The length of the channel is sufficient to accommodate the delivery chamber 60 hereafter described in its range of movement.

The inverted chamber 60 is preferably fabricated of soft molded plastic to the same width as the channel portion 41 so as to slide therein. The inverted chamber 60 has a pair of channel engaging side walls 61, and a leading side wall 62 whose sloping outer surface 63 has the same slope as the wall of the central well portion 11 so that in retracted position, shown in FIG. 1 (and in FIG. 4 in phantom lines) its sloping outer surface 63 forms a portion of one wall of the well portion 11. The inverted chamber 60 as best seen in exploded position in FIG. 2 further has a following or wiping side 64, also a recessed top 65 having one or more phantom ports 66. Said phantom ports 66 are partially spherical bores, extending from the upper surface of said recessed top 65 of the inverted chamber 60 such that the plastic between the base of said bores and the inner surface of said recessed top 65 is minimally thin.

Figure 4:
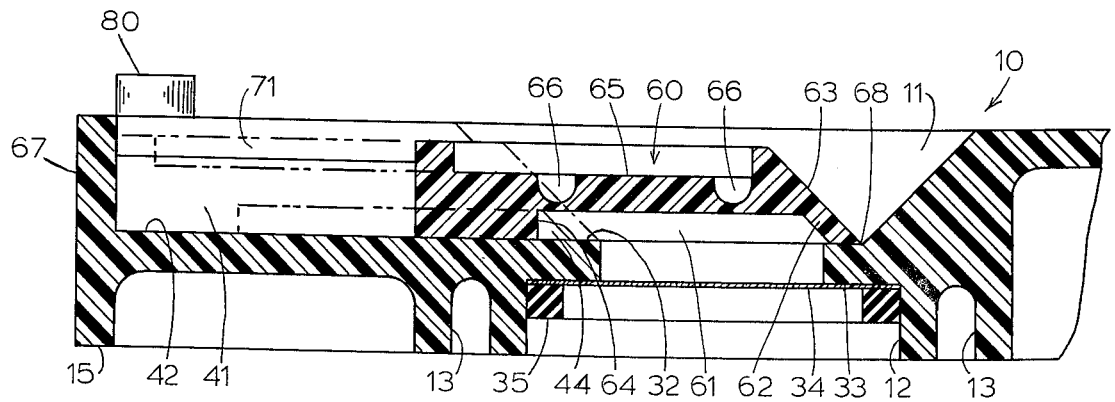
FIG. 4 is a further enlarged fragmentary sectional view corresponding to the left side of FIG. 2, showing the delivery chamber in extended position in which it serves as an incubation chamber.

The wiping side 64, as shown in FIG. 2 and FIG. 4, is somewhat elongated to fit the outer end of the channel portion 41. In retracted position shown in FIG. 2 the wiping side 64 abuts against a stop portion 67 of the body structure 10, and the lower, foremost edge 68 of the sloping retaining side 62 is aligned with the corners of the central well portion 11. The entire lower edge portions of the walls 61, 62, 64 of said inverted chamber 60 are in a plane presented in liquid sealing engagement against the horizontal surface portion 42 which thus forms the floor of a completely enclosed chamber space.

Figure 3:
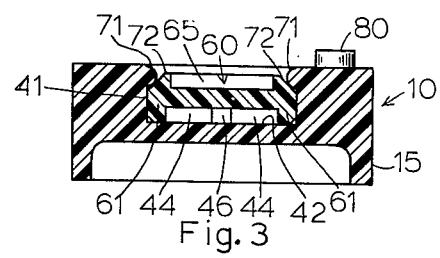
FIG. 3 is a sectional view taken along line 3—3 of FIG. 1.

The inverted chamber 60 is retained within said channel portion 41 by a bead 71 projecting inwardly from each upper inner edge of side walls 69 of said channel portion 41 as shown in FIG. 3. In the preferred embodiment the lateral upper edges 72 of said inverted chamber are beveled so that it may be easily snapped into place within said channel portion 41. So retained, said inverted chamber 60 may be slidably moved forward along said channel portion to a point at which the leading edge 68 of the retaining wall 62 encounters the upward sloping opposite wall of the central well portion 11 (FIG. 4). In such extended position a liquid contained within the chamber space formed between said inverted chamber 60 and the lower surface of said channel portion 41 is displaced downward onto said filter membrane 34. Notably, in extended position, the planar undersurfaces of the sides of said delivery chamber 60 mate with the upper surface of said flangelike frame 32 thereby forming a sealed incubation chamber.

The chamber space contains a baffle 44 projecting from the lower surface of said channel portion 41 and situated within the inner surface of said retaining side 62 of said inverted chamber 60. The baffle 44 preferably is a triangular-shaped block with a surface having the same slope as the inner surface of the retaining side 62 of said inverted chamber 60 (see broken away portion of FIG. 1). A liquid contained in said chamber space will be displaced and delivered through a central slot 46 of said baffle 44 by the inwardly sliding movement of said inverted chamber 60 from its retracted position to its extended position. Such movement of liquid through said central slot 46 causes a turbulence and consequent mixing of the liquid.

As heretofore described, the recessed top 65 of said inverted chamber 60 contains two phantom ports 66. A small gage needle may easily pierce these ports 66; hence water may be injected into one of the pierced ports 66 while air escapes from the other.

The apparatus herein described is shown with two stacking posts 80 projecting from the upper surface of said side walls of said channel portion 41 and positioned inward of its diagonally opposite corners, so as to fit within the lower exterior flanges 15 of a similar body structure placed thereabove.

An alternate embodiment of the present invention provides a second channel portion 81 in the opposite-facing wall to said retaining side of said central well portion 11 as shown in phantom lines in FIG. 1. Such second channel portion may be similarly formed in the same plane as the flange-like frame 32. A second slidable delivery chamber 82 is fitted therein and delivers a second liquid consecutively to the same said filter membrane.

The liquid contained in said inverted chamber includes a cell labeling agent. The optimal concentration of cell labeling agent for staining may be too low to prevent decay when stored in the present apparatus over long periods of time. To overcome this problem, the liquid labeling agent may be provided either as a concentrated frozen droplet or as a lyophilized film deposited upon said inverted chamber inner surface, thereby increasing the stability. Such frozen droplet is melted and diluted to the proper volume by addition of water injected by a needle after piercing the phantom ports 66 as heretofore described. Similarly the lyophilized film is dissolved and diluted by such addition of water.

In the principal use of the present invention, bacteria suspended in an aqueous sample are filtered down upon the filter membrane 34. The central well portion 11 serves as a funnel in directing downward such aqueous sample. The bacteria, retained on the surface of the filter membrane, are then stained by the liquid contained in said inverted chamber. For use in techniques which employ biological agents such as fluorescent antibodies requiring incubation, the mating of the undersurfaces of the sides of said delivery chamber 60 with the upper surface of said flangelike frame 32 provides a suitable incubation chamber and effectively prevents evaporation of the liquid labeling agent lying on said filter membrane thereunder. Following incubation, the labeling agent is filtered, and the filter membrane is washed repeatedly. Upon drying, the filter membrane may be examined directly by dark field microscopy. In a preferred embodiment, the filter membrane 34 is composed of nitrocellulose, and becomes instantly transparent to ultraviolet light when wetted with an ordinary immersion oil, conventionally used in dark field microscopy.

Thus the invention includes a new method for preparing bacterial samples for microscopic examination. The steps of the present method include storing a frozen cell-labeling agent in an inverted delivery chamber adjacent to a filter membrane mounted in a microscopic slide; and at the time of use liquifying the cell-labeling agent. Then a bacterial suspension is filtered onto the filter membrane and the liquified cell-labeling agent delivered onto the filter with the inverted delivery chamber remaining in place thereover during incubation, to serve as an incubation chamber; and finally washing and using such other slide preparation techniques as may be appropriate for the particular type of examination. So prepared the bacteria on the filter may be examined directly by ordinary microscopic techniques.

From this disclosure modifications in detailed construction and procedures will be obvious to those having ordinary skill in the art.

We claim:

1. An apparatus for use in microscopic examination of bacteria, comprising
    a microscope slide with a bore having mounted therein
    a filter mount entirely bounded by a frame part,
    a flat filter membrane having a surface which retains thereon all bacteria to be examined, mounted in said frame part without extending above the upper surface thereof, and
    a slidable inverted delivery chamber mounted sideward adjacent to said filter membrane and having a lower edge presented against the upper surface of said frame part upon the delivery chamber being slided sideward over said filter membrane, said delivery chamber being adapted to deliver a liquid to said membrane, whereby bacteria retained on the surface of said filter membrane may be treated by a liquid delivered thereon by said delivery chamber and may thereafter be examined by microscopy.

2. The apparatus as defined in claim 1 together with a cell labeling agent contained in said delivery chamber.

3. The apparatus of claim 2, wherein
said cell labeling agent is a frozen concentrated droplet maintained in said chamber at a temperature less than the melting point of said droplet, and wherein the upper wall of said chamber has a phantom port, whereby water may be introduced in order to melt said droplet and mix therewith.

4. The apparatus of claim 2, wherein the cell labeling agent is a lyophilized film on the inner surface of said chamber, and wherein the upper wall of said chamber has a phantom port, whereby water may be injected therethrough to reconstitute said lyophilized film.

5. An apparatus as defined in claim 1,
said inverted delivery chamber having a downward sloping side surface leading to said frame part,
said microscope slide further having additional surface portions sloping to said frame part which, together with said downward sloping side surface of said delivery chamber, comprise well means,
whereby the objective of a microscope may be accommodated within said well means.

6. An apparatus as defined in claim 1 wherein said microscope slide further includes
a second slidable inverted delivery chamber mounted sideward adjacent to said filter membrane opposite to the heretofore defined delivery chamber, said second delivery chamber having a lower edge similarly presented and being similarly adapted to deliver a second liquid to said membrane.

7. An apparatus as defined in claim 1, the microscope slide further having
mixing baffle means, presented upwardly within said slidable inverted delivery chamber adjacent to the said frame part bounding said filter mount, to mix such liquid as said delivery chamber is so slided sideward.

8. An apparatus as defined in claim 1 wherein
the said lower edge of said inverted delivery chamber is so sized as to seal against the upper surface of said frame part when so presented thereagainst,
whereby to provide an incubation chamber over said filter membrane.

* * * * *